United States Patent [19]  [11]  4,312,879
Lal  [45]  Jan. 26, 1982

[54] CLONIDINE AND LOFEXIDINE AS ANTIDIARRHEAL AGENTS

[75] Inventor: Harbans Lal, Kingston, R.I.

[73] Assignee: Richardson-Merrell Inc., Wilton, Conn.

[21] Appl. No.: 178,232

[22] Filed: Aug. 14, 1980

[51] Int. Cl.$^3$ ............................................ A61K 31/415
[52] U.S. Cl. ............................................... 424/273 R
[58] Field of Search ................................... 424/273 R

[56] References Cited

U.S. PATENT DOCUMENTS

| | | | |
|---|---|---|---|
| 3,190,802 | 6/1965 | Zeile et al. | 424/73 |
| 3,202,660 | 8/1965 | Zeile et al. | 424/251 X |
| 3,966,757 | 6/1976 | Baganz et al. | 424/273 X |

OTHER PUBLICATIONS

Brogden et al., Drugs 10:357–365 (1975).
Ylikorkala, Ann. Chir. Gynaecol. Fenn. 64:242–245 (1975).
Bjorkvist, Acta Psychiat. Scan. 52:256–263 (1975).
Fielding et al., J. Pharmacol. Exp. Ther. 207:899–905 (1978).
Bullock et al., Pharmacologist 20:223 (1978).
Meyer et al., Pharmacologist 18:236 (1976).
Gold et al., Lancet 2:929–930 (1978).
Washton et al., ACNP Abstracts (1978).
Drew, Proc. Brit. Pharmacol. Soc. 57P:513 (1977).
Burke et al., Clin. Pharmacol. Ther. 21:99–100 (1977).
Shearman et al., Pharmacol. Biochem. Behav. (in press).
Laverty et al., Brit. J. Pharmacol. 35:253–264 (1969).
PDR, 33rd Ed. 668. (1979).
Niemegeers et al., Synthetic Antidiarrheal Drugs, ed., Van Beaver et al., (Marcel Dekker, New York 1976) pp. 65–114.

*Primary Examiner*—Frank Cacciapaglia, Jr.
*Attorney, Agent, or Firm*—William J. Stein; Raymond A. McDonald

[57] ABSTRACT

Clonidine and lofexidine and the pharmaceutically acceptable salts thereof, which are, inter alia, known antihypertensives, also possess very potent antidiarrheal activity which is non-narcotic and more potent than that of conventional antidiarrheal drugs, such as diphenoxylate.

8 Claims, No Drawings

CLONIDINE AND LOFEXIDINE AS ANTIDIARRHEAL AGENTS

BACKGROUND OF THE INVENTION

The present invention relates to a new use of the known drugs, clonidine and lofexidine.

Clonidine, 2-(2,6-dichloroanilino)-2-imidazoline, is a widely investigated drug which is a potent antihypertensive agent, commercially available, e.g., as Catapres ® (Boehringer Ingelheim). It has also been found to alleviate migraine headache (Brogden et al, Drugs 10: 357-365, 1975), premenstrual tension (Ylikorkala. Ann. Chir. Gynaecol. Fenn. 64: 242-245, 1975) and symptoms associated with alcohol withdrawal such as tremors, sweating and anxiety (Bjorkqvist, Acta Psychiat. Scan. 52: 256-263, 1975). More recently clonidine has been reported to produce analgesia (Fielding et al, J. Pharmacol. Exp. Ther. 207: 899-905, 1978), to reduce an anxiety-related behavior (Bullock et al, Pharmacologist 20: 223, 1978), and to alleviate symptoms of narcotic withdrawal in experimental animals (Fielding et al supra and Meyer et al, Pharmacologist 18: 236, 1976) and human patients (Gold et al, Lancet 2: 929-930, 1978 and Washton et al, ACNP Abstracts, 1978). It is also known as a pilomotor agent (U.S. Patent 3,190,802 and a vasoconstrictor (U.S. Pat. No. 3,202,660). It has further been reported to inhibit intestinal cholinergic activity through stimulation of alpha-2-adrenergic receptors (Drew, Proc. Brit. Pharmacol. Soc. 57P: 513, 1977).

Lofexidine, 2-[α-(2,6-dichlorophenoxy)ethyl]-$\Delta^2$-imidazoline, is an experimental compound structurally related to clonidine. Like clonidine, lofexidine has antihypertensive activity in laboratory animals and man (Burke et al, Clin. Pharmacol. Therap. 21: 99-100, 1977). Furthermore, lofexidine was recently found to block morphine withdrawal signs in addicted rats (Shearman et al, Submitted for publication to Pharmacol. Biochem. Behav.).

Among the symptoms alleviated by these two compounds in the foregoing uses in diarrhea. For example, Meyer et al supra reported that clonidine blocked naloxone-induced diarrhea in narcotic dependent rats. Similar observations have been made by Shearman et al supra, who found clonidine to be about four times as potent as lofexidine in this regard. Clonidine has also been disclosed to reduce defecation induced by emotionality in the rat (Laverty et al, Brit. J. Pharmacol. 35: 253-264, 1969).

In these cases, the two compounds were not employed or reported as antidiarrheal agents per se. Rather, they were found to alleviate diarrhea which was a symptom of an underlying neurogenic effect being investigated with the compound. That is, in the prior art, the alleviated diarrhea was induced by central nervous system disorders.

Among the reported side effects of clonidine treatment for hypertension is constipation (P.D.R., 33rd Ed., Baker (1979), p. 558), a common side effect for very many drugs. Inducement of constipation does not establish or indicate antidiarrheal activity.

SUMMARY OF THE INVENTION

Accordingly, it is an object of this invention to provide a new use for the known compounds clonidine and lofexidine and their pharmaceutically acceptable salts.

It is another object of this invention to provide a method of treating diarrhea per se, e.g., diarrhea induced by a toxin, antigen, general irritant or by administration of an antibiotic.

Upon further study of the specification and appended claims, further objects and advantages of this invention will become apparent to those skilled in the art.

These and other objects of this invention have been attained by providing a method of treating diarrhea mediated by a toxin, an antigen, a general irritant or by administration of an antibiotic, in a patient suffering from such diarrhea and not otherwise being treated with clonidine, lofexidine or an antihypertensive drug, comprising, administering to such a patient suffering from such diarrhea, an antidiarrheally effective amount of clonidine, lofexidine or a pharmaceutically acceptable salt thereof for a period of up to 4 days and then terminating the administration.

DETAILED DISCUSSION

Clonidine and its pharmaceutically acceptable salts (e.g., U.S. Pat. No. 3,202,660), as well as lofexidine and its pharmaceutically acceptable salts (e.g., U.S. Pat. No. 3,966,757) are known compounds.

Illustrative examples of pharmaceutically acceptable salts which may be formed of clonidine and lofexidine for use in the present invention are those of any suitable inorganic acids, such as hydrochloric, hydrobromic, sulfuric or phosphoric acids or any suitable organic acid, such as carboxylic acids, such as acetic, propionic, glycolic, lactic, pyruvic, malonic, succinic, fumaric, malic, tartaric, citric, ascorbic, maleic, hydroxymaleic, benzoic, hydroxybenzoic phenylacetic, cinnamic, salicyclic, 2-phenoxybenzoic, or sulfonic acids, such as, methane sulfonic or 2-hydroxyethane sulfonic acid. The hydrochlorides are preferred.

The antidiarrheal activity of clonidine and lofexidine and their pharmaceutically acceptable salts can be established by standard pharmacological protocols such as that used in the following experiment.

Male hooded rats of the Long-Evans strain were obtained from Charles River Breeding Laboratories (Wilmington, Mass.) and housed in community cages in a room maintained at 21±1° C. They weighed 230-250 g at the time of the experiment. Food was removed the night before but water was available ad libitum. For testing, the rats were placed in individual cages and were injected i.p. with either saline or the test drug. One hour later, all of the rats were administered one ml of castor oil orally.

In a separate experiment for each drug, naloxone was also administered. This narcotic antagonist (5 mg/kg) was injected i.p. 15 minutes before as well as 15 and 45 minutes after clonidine or lofexidine injection.

At intervals of 1, 2, 3, 4, 6 and 8 hours after castor oil administration, the floor underneath each cage was examined for the presence or absence of diarrhea. Diarrhea was defined as watery and unformed stools, splashed on the tray as opposed to the normal fecal excretion that consists of wellformed boluses usually firm and fairly dry. This castor oil treatment is well-known to produce diarrhea in rats (Niemegeers et al, *Synthetic Antidiarrheal Drugs*, ed., Van Bever et al (Marcel Dekker, New York, 1976) pp. 65-114). Drug doses were calculated in terms of the hydrochloride salts. The results are summarized in the Table below.

TABLE

ANTIDIARRHEAL EFFECT OF CLONIDINE, LOFEXIDINE AND DIPHENOXYLATE IN THE RAT

| Drug | (mg/kg) | % of Rats Exhibiting Diarrhea[1] (Hours after Castor Oil) | | | | | |
|---|---|---|---|---|---|---|---|
| | | 1 | 2 | 3 | 4 | 6 | 8 |
| Saline | — | 50 | 100 | 100 | 100 | 100 | 100 |
| Clonidine | 0.01 | 16 | 100 | 100 | 100 | 100 | 100 |
| | 0.04 | 0 | 0 | 17 | 17 | 100 | 100 |
| | 0.16 | 0 | 0 | 17 | 17 | 50 | 83 |
| Clonidine[2] and Naloxone | 0.16 | 0 | 0 | 17 | 17 | — | — |
| Lofexidine | 0.01 | 67 | 100 | 100 | 100 | 100 | 100 |
| | 0.04 | 33 | 100 | 100 | 100 | 100 | 100 |
| | 0.16 | 0 | 50 | 100 | 100 | 100 | 100 |
| | 0.32 | 0 | 17 | 32 | 67 | 83 | 100 |
| | 0.64 | 0 | 0 | 0 | 17 | 33 | 83 |
| Lofexidine[2] and Naloxone | 0.16 | 17 | 33 | 100 | 100 | 100 | 100 |
| Diphenoxylate (prior art) | 0.04 | 95 | 100 | 100 | 100 | 100 | 100 |
| | 0.16 | 60 | 90 | 100 | 100 | 100 | 100 |
| | 0.64 | 0 | 50 | 65 | 80 | 90 | 95 |

[1]Eighteen rats were used for saline and six rats for each dose of lofexidine and clonidine. Diphenoxylate data were obtained from Niemegeers et al supra.
[2]Animals were treated with naloxone (5 mg/kg) 15 min before as well as 15 min and 45 min after lofexidine (0.16 mg/kg) or clonidine (0.16 mg/kg). All drugs were injected i.p.

These data show that the castor oil treatment induced diarrhea in all of the rats pretreated with saline. Pretreatment with clonidine or lofexidine, however, produced a dose-dependent inhibition of the diarrhea, demonstrating that they both produce a potent antidiarrheal action. Equivalent data is also included in the Table for the known antidiarrheal, diphenoxylate which is one of the most effective current antidiarrheal agents. It can be seen from this data that both clonidine and lofexidine are much more potent, on a weight basis, than diphenoxylate. Furthermore, both drugs show a considerably longer duration of action than diphenoxylate.

In contrast to the known antagonism of diphenoxylate-type antidiarrheals by naloxone, both pretreatment and posttreatment of clonidine- or lofexidinetreated rats with naloxone failed to either block or antagonize the antidiarrheal action of these drugs. Consequently, these compounds provide potent antidiarrheal activity which is of a non-narcotic nature.

These data are especially significant in view of the facts that clonidine is a non-narcotic drug with an established record of clinical safety and that clonidine displays antidiarrheal activity at doses presently considered nontoxic. Further, the data also show that lofexidine displays antidiarrheal activity at doses which lack toxicity as indicated by known animal and clinical data, (Burke et al supra).

Clonidine, lofexidine and their pharmaceutically acceptable salts are thus useful for treating a wide range of diarrheas, i.e., caused by a broad spectrum of mediators (listed below in most cases with the putative mechanism), including those mediated by toxins, e.g., enterotoxins such as Vibrio cholera and *Escherichia coli* (for which adenyl cyclase stimulation results in increased fluid production), Salmonella and Shigelia species (inflammatory; mucosal damage), Clostridium and Kiebsiella species and viral agents, such as orbivirus, Coxsackie, Echo, Norwalk, etc.; those mediated by antigens such as *S. aureus* and *C. perfringens* (antigenic toxin causes excess fluid production); those mediated by general irritants; and also those resulting from administration of antibiotics such as broad spectrum antibiotics, e.g., tetracyclines, (alteration in intestinal flora), and Clindamycin and Lincomycin which are especially notorious (producing overgrowth of *C. difficile*).

The compounds of this invention may be administered to warm-blooded animals including mammals, such as dogs, cats, rats, horses, bovine cows, mice, pigs, goats, sheep and humans and birds, such as chickens and turkeys. The compounds may be administered alone or may be used in combination with antibiotics, such as antibacterial agents, for example, clindamycin, lincomycin, tetracycline and cephalosporins used in general therapy or for the treatment of the enterotoxins. The compounds may also be used with other antisecretory agents, such as diphenoxylate and atropine, and with electrolyte solutions serving as fluid replacement or maintenance therapy. The compounds of this invention may be administered alone or in the form of pharmaceutical preparations and may be administered orally or parenterally, for example, intravenously and intraperitoneally. Oral administration is preferred. Pharmaceutical preparations containing conventional pharmaceutical carriers and as active ingredients, the compounds of this invention can be employed in unit dosage forms such as solids, for example, tablets, capsules and pills or liquid solutions, suspensions and emulsions for oral and parenteral administration.

The amount of compound administered can be any antidiarrheally effective amount. The dosage unit administered can vary over a wide range. To be clinically useful in the management of diarrhea, the effective dose for both drugs should lie between 0.1 and 0.4 mg. daily (0.05 to 0.2 mg. b.i.d.). Unit doses may contain from about 0.05 mg to 0.4 mg of the compound as appropriate for administration, for example, from 1 to 4 times daily. In addition, the compounds may be administered alone or concurrently, sequentially or serially with other agents as mentioned above. As used herein, the term patient is intended to mean the animal or mammal being treated.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

An illustrative composition for tablets is the following:

|   |   | mg/tablet |
|---|---|---|
| (a) | Clonidine or Lofexidine | 0.1 |
| (b) | Lactose | 33 |
| (c) | Corn starch | 11.25 |
| (d) | Sucrose 3% starch | 12.75 |
| (e) | Corn starch paste (10%) | 1.50 |
| (f) | Zinc stearate | 1.50 |

The dry lactose, corn starch and sucrose 3% starch are screened through a 30-mesh screen and blended. The powder mix is granulated with 10% corn starch paste, and the wet granulation is passed through a No. 4 screen and dried. The dried granulation is screened and blended with the zinc stearate which also is screened, and the resulting mixture is compressed into tablets weighing 60.1 mg each.

EXAMPLE 2

An enteric coated tablet is afforded when a tablet formulated as in EXAMPLE 1 is sprayed with a 4% solution of hydroxypropyl methylcellulose phthalate increasing the weight of the tablet about 6 mg.

EXAMPLE 3

An illustrative sterile aqueous solution suitable for parenteral use is prepared from the following ingredients:

|   |   | Grams |
|---|---|---|
| (a) | Clonidine or Lofexidine | 0.01 |
| (b) | Polyethylene glycol 4000, U.S.P. | 3 |
| (c) | Sodium chloride | 0.9 |
| (d) | Polyoxyethylene derivatives of sorbitan monooleate (TWEEN 80) U.S.P. | 0.4 |
| (e) | Sodium metabisulfite | 0.1 |
| (f) | Methylparaben, U.S.P. | 0.18 |
| (g) | Propylparaben, U.S.P. | 0.02 |
| (h) | Water for injection q.s. to 100 ml | |

The parabens, sodium metabisulfite and sodium chloride are dissolved in approximately one-half the volume of water for injection at 80° C. with stirring. The solution is cooled to below 40° C. and the active ingredient is dissolved therein followed by the polyethylene glycol 4,000 and the polyoxyethylene derivatives of sorbitan monooleate. The cooled solution is adjusted to the final volume with water for injection and is then sterilized by sterile filtration through a suitable filter. Each one ml of solution contains 0.1 mg of the acti

EXAMPLE 4

An illustrative capsule preparation is the following. One thousand twopiece hard gelatin capsules for oral use each containing 0.1 mg of the active ingredient are prepared from the following ingredients:

|   |   | Grams |
|---|---|---|
| (a) | Clonidine or Lafexidine | 0.1 |
| (b) | Lactose, U.S.P. | 100 |
| (c) | Starch, U.S.P. | 10 |
| (d) | Talc, U.S.P. | 5 |
| (e) | Calcium stearate | 1 |

The finely powdered materials are mixed until uniformly dispersed and filtered into hard shelled gelatin capsules of the appropriate size.

In a similar fashion one-piece soft gelatin capsules can be prepared in which the above formulation can be granulated slugged or compressed directly into a rotary die or plate mold in which the capsule is formed. Alternatively, the above excipients may be omitted and the active ingredient dispensed as a powder directly into the capsule.

EXAMPLE 5

As shown above, clonidine, lofexidine and their salts can be administered to a patient as antidiarrheal agents for the treatment of diarrhea induced by a wide variety of causes, e.g., by toxins, antigens, irritants or by administration of antibiotics.

As the experimental results summarized above establish, the compounds of this invention display antidiarrheal effects in rats under conditions comparable to those under which administration of the known antidiarrheal agent diphenoxylate achieves antidiarrheal effects. Thus, the compounds of this invention will be administered to humans for the same indications, for example, as those seen in rats for diphenoxylate.

Of course, the dosage amounts for the compounds of this invention will be adjusted for their increased potency compared with that of diphenoxylate as shown, e.g., in the Table above. Furthermore, since the compounds of this invention are indicated to be non-narcotic, the severity of control required in the administration of diphenoxylate is not needed. Rather, administration of the compounds of this invention as antidiarrheals is analogous to that for the same drugs employed in their other known uses, e.g., as antihypertensives, except that the administration of these compounds as antidiarrheals should not be continued as for an antihypertensive. Rather, administration should be for a limited period, e.g., for up to 4 days and then treatment should be terminated. In this way, potential adverse effects due to abrupt termination, e.g., of clonidine, after such prolonged use, will be minimized, as will be the potential for development of patient tolerance. Moreover, the compounds of this invention should not be administered as antidiarrheal agents to patients already on an antihypertensive drug, e.g., clonidine or lofexidine, or on clonidine or lofexidine for any other reason.

For example, clonidine or lofexidine hydrochloride can be administered orally to a 70 kg adult in a total daily dose of about 0.4 mg, administered in the corresponding requisite unit doses 1–4 times daily.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of alleviating the symptoms of diarrhea induced by a toxin, antigen, a general irritant or by the administration of an antibiotic, but excluding diarrhea induced by central nervous system disorders, in a patient not otherwise being treated with clonidine, lofexidine or an antihypertensive drug, comprising administering to such a patient an antidiarrheally-effective, non-antihypertensive amount of clonidine, lofexidine or a pharmaceutically acceptable salt thereof for a period of up to 4 days.

2. The method of claim 1, wherein clonidine is administered to the patient.

3. The method of claim 1, wherein lofexidine is administered to the patient.

4. The method of claim 2, wherein clonidine is administered as its hydrochloride salt.

5. The method of claim 3, wherein lofexidine is administered as its hydrochloride salt.

6. The method of claim 2, wherein the dosage of clonidine is 0.1–0.4 mg per day.

7. The method of claim 3, wherein the dosage of lofexidine is 0.1–0.4 mg per day.

8. The method of claim 1, wherein the administration is oral.

* * * * *